(12) United States Patent
Gale

(10) Patent No.: US 8,663,680 B2
(45) Date of Patent: *Mar. 4, 2014

(54) TRANSPARENT TRANSDERMAL NICOTINE DELIVERY DEVICES

(75) Inventor: Robert M. Gale, Los Altos, CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/311,437

(22) Filed: Dec. 5, 2011

(65) Prior Publication Data

US 2012/0310187 A1     Dec. 6, 2012

Related U.S. Application Data

(63) Continuation of application No. 11/841,789, filed on Aug. 20, 2007, now Pat. No. 8,075,911, which is a continuation of application No. 10/871,458, filed on Jun. 18, 2004, now Pat. No. 7,622,136, which is a continuation of application No. 09/464,305, filed on Dec. 15, 1999, now abandoned.

(60) Provisional application No. 60/112,730, filed on Dec. 18, 1998, provisional application No. 60/124,679, filed on Mar. 16, 1999, provisional application No. 60/126,798, filed on Mar. 30, 1999.

(51) Int. Cl.
*A61F 13/00* (2006.01)
*A61F 13/02* (2006.01)

(52) U.S. Cl.
USPC .......................... 424/449; 424/443; 424/448

(58) Field of Classification Search
None
See application file for complete search history.

(56) References Cited

U.S. PATENT DOCUMENTS

| | | | |
|---|---|---|---|
| 3,598,122 A | 8/1971 | Zaffaroni | |
| 3,598,123 A | 8/1971 | Zaffaroni | |
| 3,731,683 A | 5/1973 | Zaffaroni | |
| 3,797,494 A | 3/1974 | Zaffaroni | |
| 3,995,631 A | 12/1976 | Higuchi et al. | |
| 4,031,894 A | 6/1977 | Urquhart et al. | |
| 4,144,314 A | 3/1979 | Dorges et al. | |
| 4,144,317 A | 3/1979 | Higuchi et al. | |
| 4,201,211 A | 5/1980 | Chandrasekaran et al. | |
| 4,203,440 A | 5/1980 | Theeuwes | |
| 4,286,592 A | 9/1981 | Chandrasekaran | |
| 4,314,557 A | 2/1982 | Chandrasekaran | |
| 4,327,725 A | 5/1982 | Cortese et al. | |
| 4,373,454 A | 2/1983 | Pitrolo et al. | |
| 4,379,454 A | 4/1983 | Campbell et al. | |
| 4,435,180 A | 3/1984 | Leeper | |
| 4,559,222 A | 12/1985 | Enscore et al. | |
| 4,568,343 A | 2/1986 | Leeper et al. | |
| 4,573,995 A | 3/1986 | Cheng et al. | |
| 4,588,580 A | 5/1986 | Gale et al. | |
| 4,597,961 A | 7/1986 | Etscorn | |
| 4,612,008 A | 9/1986 | Wong et al. | |
| 4,627,850 A | 12/1986 | Deters et al. | |
| 4,645,502 A | 2/1987 | Gale et al. | |
| 4,698,062 A | 10/1987 | Gale et al. | |
| 4,704,282 A | 11/1987 | Campbell et al. | |
| 4,725,272 A | 2/1988 | Gale | |
| 4,758,434 A | 7/1988 | Kydonieus et al. | |
| 4,764,382 A | 8/1988 | Kydonieus et al. | |
| 4,765,989 A | 8/1988 | Wong et al. | |
| 4,781,924 A | 11/1988 | Lee et al. | |
| 4,783,337 A | 11/1988 | Wong et al. | |
| 4,788,062 A | 11/1988 | Gale et al. | |
| 4,816,258 A | 3/1989 | Nedberge et al. | |
| 4,839,174 A | 6/1989 | Baker et al. | |
| 4,849,226 A | 7/1989 | Gale | |
| 4,904,475 A | 2/1990 | Gale et al. | |
| 4,908,027 A | 3/1990 | Enscore et al. | |
| 4,908,213 A | 3/1990 | Govil et al. | |
| 4,915,950 A | 4/1990 | Miranda et al. | |
| 4,917,895 A | 4/1990 | Lee et al. | |
| 4,938,759 A | 7/1990 | Enscore et al. | |
| 4,943,435 A | 7/1990 | Baker et al. | |
| 4,946,853 A | 8/1990 | Bannon et al. | |
| 5,004,610 A | 4/1991 | Osborne et al. | |
| 5,016,652 A | 5/1991 | Rose et al. | |
| 5,071,656 A | 12/1991 | Lee et al. | |
| 5,077,104 A | 12/1991 | Hunt et al. | |
| 5,122,382 A | 6/1992 | Gale et al. | |
| 5,141,750 A | 8/1992 | Lee et al. | |
| 5,167,649 A | 12/1992 | Zook | |
| 5,230,896 A | 7/1993 | Yeh et al. | |
| 5,284,660 A | 2/1994 | Lee et al. | |
| 5,314,694 A | 5/1994 | Gale et al. | |

(Continued)

FOREIGN PATENT DOCUMENTS

| | | |
|---|---|---|
| CA | 2250025 | 10/1997 |
| EP | 0338819 | 10/1989 |
| EP | 0563507 | 5/1998 |
| GB | 2148712 | 6/1985 |
| GB | 2182559 | 5/1987 |
| GB | 2184016 | 6/1987 |
| JP | 05632414 | 8/1979 |
| JP | 60069014 | 4/1985 |
| JP | 07165563 | 6/1995 |
| JP | 09323925 | 12/1997 |

(Continued)

OTHER PUBLICATIONS

U.S. Appl. No. 09/464,305, filed Dec. 15, 1999, Gale.
Wang, et al., "Surface Nature of UV Deterioration in Properties of Solid Poly (ethylene terephthalate)." J. Applied Poly. Sci., 1998, 67, pp. 706-714.
"Drug Patches Catch On" Chembytes e-Zine, Oct. 1995.

(Continued)

*Primary Examiner* — Brian Gulledge
(74) *Attorney, Agent, or Firm* — Stoel Rives, LLP; Samuel E. Webb; Zhi-Xiang (Alex) Oh

(57) ABSTRACT

A transparent transdermal delivery device for delivering nicotine which has an Opacity Index of less than 48.6%.

9 Claims, No Drawings

(56) References Cited

U.S. PATENT DOCUMENTS

| | | | |
|---|---|---|---|
| 5,324,280 A | 6/1994 | Wong et al. | |
| 5,342,623 A | 8/1994 | Enscore et al. | |
| 5,344,656 A | 9/1994 | Enscore et al. | |
| 5,364,630 A | 11/1994 | Osborne et al. | |
| 5,372,819 A * | 12/1994 | Godbey et al. | 424/449 |
| 5,411,739 A | 5/1995 | Jaeger et al. | |
| 5,411,740 A | 5/1995 | Lee et al. | |
| 5,462,745 A | 10/1995 | Enscore et al. | |
| 5,508,038 A | 4/1996 | Wang et al. | |
| 5,599,554 A | 2/1997 | Majeti | |
| 5,603,947 A | 2/1997 | Wong et al. | |
| 5,626,866 A * | 5/1997 | Ebert et al. | 424/447 |
| 5,635,203 A | 6/1997 | Gale et al. | |
| 5,721,257 A | 2/1998 | Baker et al. | |
| 5,726,190 A | 3/1998 | Rose et al. | |
| 5,976,565 A | 11/1999 | Fotinos | |
| 6,010,715 A | 1/2000 | Wick et al. | |
| 6,013,722 A | 1/2000 | Yang | |
| 6,027,748 A | 2/2000 | Conte et al. | |
| 6,203,817 B1 | 3/2001 | Cormier et al. | |
| 6,512,010 B1 | 1/2003 | Gale et al. | |
| 6,562,363 B1 | 5/2003 | Mantelle et al. | |
| 8,075,911 B2 | 12/2011 | Gale | |
| 2008/0031933 A1 | 2/2008 | Gale | |

FOREIGN PATENT DOCUMENTS

| | | |
|---|---|---|
| JP | 10279472 | 10/1998 |
| WO | WO 91/09592 | 7/1991 |
| WO | WO 91/09731 | 7/1991 |
| WO | WO 9115196 | 10/1991 |
| WO | WO 95/24172 | 9/1995 |
| WO | WO 97/33581 | 9/1997 |
| WO | WO 00/37058 | 6/2000 |

OTHER PUBLICATIONS

Doctor's Guide "Clear NicoDerm Now Available in US" http://www.psigroup.com/dg/lcd502.htm Aug. 21, 2006 pp. 1-3.

Chembytes e-Zine "Drug Patches Catch On" http://64.233.169.104/search?q=cache:cokDhB0xGoJ:www.chemsoc.org/chembytes/ezine Oct. 9, 2007 pp. 1-8.

First Office Action issued Jun. 9, 2000 in U.S. Appl. No. 09/464,305.

Final Office Action issued Dec. 13, 2000 in U.S. Appl. No. 09/464,305.

Non-Final Office Action issued Jul. 12, 2001 in U.S. Appl. No. 09/464,305.

Final Office Action issued Feb. 25, 2002 in U.S. Appl. No. 09/464,305.

Office Action issued Mar. 24, 2004 in U.S. Appl. No. 09/464,305.

First Office Action issued Jun. 1, 2005 in U.S. Appl. No. 10/871,458, now US Patent No. 7622136.

Second Office Action issued Nov. 21, 2005 in U.S. Appl. No. 10/871,458, now US Patent No. 7622136.

Final Office Action issued Apr. 11, 2006 in U.S. Appl. No. 10/871,458, now US Patent No. 7622136.

Non-Final Office Action issued Oct. 17, 2006 in U.S. Appl. No. 10/871,458, now US Patent No. 7622136.

Final Office Action issued May 17, 2007 in U.S. Appl. No. 10/871,458, now US Patent No. 7622136.

Non-Final Office Action issued Oct. 15, 2007 in U.S. Appl. No. 10/871,458, now US Patent No. 7622136.

Final Office Action issued Apr. 7, 2008 in U.S. Appl. No. 10/871,458, now US Patent No. 7622136.

Amendment After Allowance filed Apr. 22, 2009 in U.S. Appl. No. 10/871,458, now US Patent No. 7622136.

Notification of Transmittal of the International Search Report issued Apr. 26, 2000 in International Application No. PCT/US1999/029731.

Written Opinion issued Sep. 11, 2000 in International Application No. PCT/US1999/029731.

Notification of Transmittal of the International Preliminary Examination Report issued Jan. 31, 2001 in International Application No. PCT/US1999/029731.

Extended European Search Report issued Mar. 12, 2010 in European Divisional Application No. 09174885.5.

Preliminary Amendment filed Aug. 20, 2007 in co-pending U.S. Appl. No. 11/841,789, now US Patent No. 8,075,911.

First Office Action issued Jul. 31, 2008 in co-pending U.S. Appl. No. 11/841,789, now US Patent No. 8,075,911.

Response to Jul. 31, 2008 Office Action filed Oct. 31, 2008 in co-pending U.S. Appl. No. 11/841,789, now US Patent No. 8,075,911.

Office Action issued Feb. 5, 2009 in co-pending U.S. Appl. No. 11/841,789, now US Patent No. 8,075,911.

Interview Summary issued May 6, 2009 in co-pending U.S. Appl. No. 11/841,789, now US Patent No. 8,075,911.

Response to Feb. 5, 2009 Office Action filed Jun. 3, 2009 in co-pending U.S. Appl. No. 11/841,789, now US Patent No. 8,075,911.

Office Action issued Aug. 19, 2009 in co-pending U.S. Appl. No. 11/841,789, now US Patent No. 8,075,911.

Notice of Appeal filed Nov. 19, 2009 in co-pending U.S. Appl. No. 11/841,789, now US Patent No. 8,075,911.

Applicant's Appeal Brief filed Jan. 19, 2010 in co-pending U.S. Appl. No. 11/841,789, now US Patent No. 8,075,911.

Examiner's Answer to Applicant's Appeal Brief filed Apr. 9, 2010 in co-pending U.S. Appl. No. 11/841,789, now US Patent No. 8,075,911.

Applicant's Reply Brief filed Jun. 9, 2010 in co-pending U.S. Appl. No. 11/841,789, now US Patent No. 8,075,911.

Decision on Appeal issued May 25, 2011 in co-pending U.S. Appl. No. 11/841,789, now US Patent No. 8,075,911.

Interview Summary issued Jul. 7, 2011 in co-pending U.S. Appl. No. 11/841,789, now US Patent No. 8,075,911.

Hartley, D., Kidd, H. (eds.); "The Agrochemical Handbook." The Royal Society of Chemistry United Kingdom (1985).

Eatough, et al., "Chemical Composition of Environmental Tobacco Smoke." Environ. Sci. Technol., 1989, 23 (6) p. 685.

McEvoy, D. J. (ed.); American Hospital Formulary Service—Drug Information 97. Bethesda, MD: American Society of Health-System Pharmacists, Inc. 1997, p. 1050.

Gorrod, J. W., Jacob III, P. (eds.); Analytical Determination of Nicotine and Related Compounds and Their Metabolites Elsevier (1999) p. 78.

Response to First Office Action filed Nov. 16, 2000 in U.S. Appl. No. 09/464,305.

Response to Final Office Action filed Jun. 12, 2001 in U.S. Appl. No. 09/464,305.

Response to Non-Final Office Action filed Jan. 9, 2002 in U.S. Appl. No. 09/464,305.

Preliminary Amendment filed Jun. 18, 2004 in U.S. Appl. No. 10/871,458, now US Patent No. 7622136.

Preliminary Amendment filed Jan. 4, 2005 in U.S. Appl. No. 10/871,458, now US Patent No. 7622136.

Response to First Office Action issued Sep. 1, 2005 in U.S. Appl. No. 10/871,458, now US Patent No. 7622136.

Response to Second Office Action issued Jan. 18, 2006 in U.S. Appl. No. 10/871,458, now US Patent No. 7622136.

Response to Final Office Action issued Jun. 8, 2006 in U.S. Appl. No. 10/871,458, now US Patent No. 7622136.

Advisory Action issued Jun. 16, 2006 in U.S. Appl. No. 10/871,458, now US Patent No. 7622136.

Request for Continued Examination filed Aug. 3, 2006 in U.S. Appl. No. 10/871,458, now US Patent No. 7622136.

Response to Non-Final Office Action filed Feb. 16, 2007 in U.S. Appl. No. 10/871,458, now US Patent No. 7622136.

Response to Final Office Action filed Jul. 25, 2007 in U.S. Appl. No. 10/871,458, now US Patent No. 7622136.

Response to Non-Final Office Action filed Jan. 10, 2008 2007 in U.S. Appl. No. 10/871,458, now US Patent No. 7622136.

Examiner Interview Summary issued Feb. 27, 2008 in U.S. Appl. No. 10/871,458, now US Patent No. 7622136.

Applicant Interview Summary filed Mar. 21, 2008 in U.S. Appl. No. 10/871,458, now US Patent No. 7622136.

(56) References Cited

OTHER PUBLICATIONS

Response to Final Office Action filed May 6, 2008 in U.S. Appl. No. 10/871,458, now US Patent No. 7622136.
Advisory Action issued May 16, 2008 in U.S. Appl. No. 10/871,458, now US Patent No. 7622136.
Appeal Brief filed Jun. 25, 2008 in U.S. Appl. No. 10/871,458, now US Patent No. 7622136.
"3M 9733 Scotchpak Polyester Film Laminate," Extract from Online Product Catalog, 1 pg., (2011).
"3M Scotchpak 9733 Backing," 3M Drug Delivery Systems, pp. 1-2, (Oct. 2004).
"Rods, Tubes & Profiles, Nylon 6/6 Rod," http://www.polyzone.com/products/rods-tubes-profiles/nylon-6-6-rod, 1 pg., (Feb. 11, 2012).
Picture of Macbeth 1500/Plus color measurement system, 1 pg., retrieved Dec. 20, 2012.
"Florida Administrative Code & Register," eRegulations, http://florida.eregulations.us/code/rulehome/04/13/2012/20-65.002.html, 1 pg., (2011).
"Color-Eye7000A Spectrophotometer: Operation Manual," x-rite, 1 pg., retrieved Dec. 20, 2012.
"Color i7 Benchtop Spectrophotometer: Operation Manual," x-rite, P/N. 391232, Ver. 2, 26 pgs., (Apr. 2009).
"Color i5 Benchtop Spectrophotometer: Operation Manual," x-rite, Ver. 2, 27 pgs., (Dec. 2011).
"Datacolor 650™, 600™, 400™ User's Guide," Datacolor, Part No. 4230-0395M, Rev. 1, 54 pgs., (Jan. 2007).
"UltraScan Pro Product Brochure," HunterLab, 6 pgs., (May 2006).
Wu et al., "Novel Microporus Films and Their Composites," Journal of Engineered Fibers and Fabrics, vol. 2, Issue 1, pp. 49-59, (2007).
"Stability Study 2476 Excerpt from Transparent Transdermal Nicotine Delivery Devices" Annex 4—Written Submissions in Response to the Summons to Attend Oral Proceedings, 5 pgs., (Oct. 21, 2008).
"DANISCO A/S and Another v NOVOZYMES A/S and Another (No. 2)," Federal Court of Australia, Annexure C, pp. 209-213 and 260-266, (2011).
Swain et al., "Ultraviolet Absorption Spectra of Nicotine, Nornicotine and Some of Their Derivatives", vol. 71, pp. 1341-1345, (Apr. 1949).

\* cited by examiner

TRANSPARENT TRANSDERMAL NICOTINE DELIVERY DEVICES

CLAIM OF PRIORITY

This application is a continuation of U.S. application Ser. No. 11/841,789, filed Aug. 20, 2007, which is a continuation of U.S. application Ser. No. 10/871,458, filed Jun. 18, 2004, which is a continuation of U.S. application Ser. No. 09/464,305, filed Dec. 15, 1999, which claims the benefit of U.S. provisional patent applications Nos. 60/112,730, filed Dec. 18, 1998; 60/124,679, filed Mar. 16, 1999; and 60/126,798, filed Mar. 30, 1999, all of which are incorporated herein by reference.

FIELD OF THE INVENTION

The present invention relates to transdermal delivery devices for administering nicotine for use in smoking cessation treatments. In particular, the invention is directed to transdermal nicotine delivery devices which are transparent.

BACKGROUND OF THE INVENTION

The transdermal route of parenteral drug delivery provides many advantages over other administration routes. Transdermal systems for delivering a wide variety of drugs or other beneficial agents are described in U.S. Pat. Nos. 3,598,122; 3,598,123; 3,731,683; 3,797,494; 4,031,894; 4,144,317; 4,201,211; 4,286,592; 4,314,557; 4,379,454; 4,435,180; 4,559,222; 4,568,343; 4,573,995; 4,588,580; 4,645,502; 4,698,062; 4,704,282; 4,725,272; 4,781,924; 4,788,062; 4,816,258; 4,849,226; 4,904,475; 4,908,027; 4,917,895; 4,938,759; 4,943,435; 5,004,610; 5,071,656; 5,122,382; 5,141,750; 5,284,660; 5,314,694; 5,342,623; 5,411,740; and 5,635,203, which are hereby incorporated in their entirety by reference.

The administration of nicotine buccally, nasally and transdermally to assist a patient desiring to quit smoking has been shown to be clinically effective in reducing the rate of recidivism. Nicotine chewing gum and transdermal nicotine are two of the most widely used forms of nicotine replacement therapy currently available. Transdermal devices for administering nicotine are disclosed in U.S. Pat. Nos. 4,597,961; 4,758,434; 4,764,382; 4,839,174; 4,908,213; 4,915,950; 4,943,435; 4,946,853; 5,004,610; 5,016,652; 5,077,104; 5,230,896; 5,411,739; 5,462,745; 5,508,038; 5,599,554; 5,603,947 and 5,726,190, for example, which are hereby incorporated in their entirety by reference.

Most of the transdermal drug delivery devices of the prior art utilize an impermeable backing on the skin distal surface of the device to protect the device from damage and to prevent loss of the active ingredient(s). In order to improve user satisfaction, these backing layers are often tinted to a color similar to skin tones. However, as can be readily appreciated, it is not commercially practical to provide pigmented backing layers for transdermal systems which approximate all skin colors.

Another approach that has been taken is to provide transparent transdermal systems in which all elements forming a device are sufficiently transparent to permit the natural skin color to be visible through the device. Marketed products which take this approach include the ALORA® and CLIMARA® estrogen replacement patches and the DURAGESIC® transdermal fentanyl delivery system. When these devices are applied to the skin, the patient's natural skin color is visible through the patch, making the presence of the patch extremely inconspicuous. Government regulations require that these products bear identifying indicia, but the indicia can be printed on these devices in light colored or white ink which is not noticeable from a distance of several feet, but is still readable on close inspection.

Such transparent patches have been found useful with non-volatile drugs such as fentanyl and hormone replacement steroids, but no such transparent product has been developed for the delivery of nicotine.

Nicotine is a liquid alkaloid that is colorless, volatile, strongly alkaline, readily oxidized, subject to degradation on exposure to light and highly permeable through not only the human skin, but also many of the polymers conventionally used in the fabrication of backing layers and packaging materials for transdermal products (see for example U.S. Pat. No. 5,077,104). As a result, the backing layers of the transdermal nicotine delivery devices currently available utilize opaque, skin-colored multilaminate films which typically contain a metalized layer, such as aluminum.

Not only do the commercially available transdermal nicotine patches use opaque backings, but many of these devices, due to the complexities of handling and processing nicotine, have other components which are not transparent. For example, the original Prostep® transdermal nicotine product used a drug reservoir in the form of an opaque white gel, held in place by an opaque adhesive overlay. The HABITROL® and NICOTROL® nicotine patches incorporated absorbent pads in the drug reservoir in which the nicotine was absorbed.

It has also been proposed to co-administer nicotine with other substances that improve nicotine cessation therapy. See, for example, U.S. Pat. Nos. 4,908,213; 5,599,554; and 5,726,190 noted above; and WO 97/33581.

SUMMARY OF THE INVENTION

The present invention relates to transparent transdermal delivery devices for the transdermal administration of nicotine, either alone or in combination with other agents.

Such devices should be sufficiently transparent so that the subject's skin can be clearly visible through the device when it is placed on the skin. Identifying indicia can be printed on the device in light colored or white ink in a manner which is not noticeable from a short distance, but is readable on close inspection.

DETAILED DESCRIPTION OF THE INVENTION

Preferred devices of this invention utilize, as the backing layer, a transparent polymeric film which has a permeability to nicotine of less than 1 $\mu g/cm^2/hr$, preferably less than 0.5 $\mu g/cm^2/hr$, a solubility for nicotine that is less than 1% by weight and preferably less than 0.1%. Such films are preferably less than about 6 mils thick and most preferably about 2-4 mils thick. Such films are used in combination with one or more of the conventional elements of a transdermal device (other than the removable release liner) such as the drug reservoir, adhesive and rate controlling membranes, which must also be sufficiently transparent as to permit the natural skin color to be clearly visible through the assembled device after placement on the skin. The finished product should have an Opacity Index of less than about 48.6%, preferably less than about 35.11% and more preferably less than 20%.

In addition to being transparent and being sufficiently impermeable to nicotine, the backing layer must also have sufficient mechanical strength and physical integrity to maintain the system intact throughout its intended administration period, which is typically 18-24 hours, and must provide a stable interface with adjoining layers such as the drug reservoir or adhesive layers of the transdermal device. This combination of properties is not always found in one material, and thus the transparent backing layers used on the devices of this invention can be multilaminate films. In addition to having a low permeability to nicotine, a backing layer must also have a low solubility for nicotine. This is because nicotine is toxic and it could be dangerous for a child, for example, to lick the backing layer if it contained a substantial amount of dissolved nicotine.

Suitable polymer materials possessing properties required by this invention include SCOTCHPAK® 1220 film, which is a polyethylene terephthalate/ethylene vinyl acetate (PET EVA), bilaminate film sold by the 3M Company, Minneapolis, Minn., and SARANEX® 2057 film, which is a high density polyethylene (HDPE)/ethylene acrylic acid (EAA)/nylon/EAA multilaminate available from the Dow Chemical Company, Midland, Mich. Nitrile rubber graft copolymers with acrylonitrile and methyl acrylate sold as Barex® films described in U.S. Pat. No. 5,077,104 noted above, can also be used.

These films, comprising a graft copolymer formed from about 73-77% acrylonitrile and from about 23-27% methyl acrylate copolymerized in the presence of about 8-10 parts by weight of butadiene/acrylonitrile copolymers containing approximately 70% by weight of polymer units derived from butadiene are preferred backing materials.

The transparent transdermal delivery devices of this invention can be of any of the forms described in the aforementioned patents. The preferred form, however, comprises a laminate of the backing layer, a nicotine reservoir layer which contains nicotine dissolved in a carrier at a concentration below the saturation concentration of nicotine in the carrier. If the drug reservoir component is self adhesive, a simple monolithic device could be employed. However, in many cases it is desirable to include additional components such as rate controlling membranes, and a separate adhesive layer for maintaining the devices on the skin such as is described in U.S. Pat. Nos. 5,004,610 and 5,342,623 listed above. It is further contemplated that in addition to nicotine, the device may also contain other drugs or other active substances which cooperate with or enhance the effect of nicotine in smoking cessation, smoking replacement or smoking substitution therapy. For all these devices, a removable release liner would normally be applied on the adhesive surface of the patch that is used to keep the device on the skin, which release liner is removed prior to use.

Various materials suited for fabrication of the various components are known in the art and are disclosed in the aforementioned patents.

The adhesive component is preferably a pressure sensitive adhesive including, but not limited to, polysiloxanes, polyacrylates, polyurethanes, acrylic adhesives including cross linked or uncross linked acrylic copolymers, vinyl acetate adhesives, ethylene vinylacetate copolymers, and natural or synthetic rubbers including polybutadienes, polyisoprenes, and polyisobutylene adhesives, and mixtures and graft copolymers thereof. The devices may also be provided with hydrophilic water absorbing polymers known in the art such as polyvinyl alcohol and polyvinyl pyrolidone individually or in combination. The adhesive can be used to form a monolithic delivery device in which the nicotine is dissolved in the adhesive to form a self-adhesive drug reservoir. Alternatively, the adhesive can be applied to the surface of a non-adhesive reservoir in which nicotine is dissolved, to form a multilaminate device. A rate-controlled membrane can also be interfaced between the nicotine reservoir and the adhesive, as is known to the art.

The nicotine can be administered in combination with another agent which could include anti-anxiolytics, antihypertensives, antidepressants, and appetite suppressants, such as fluoxetine, caffeine, buspirone, phenylpropanolamine, clonidine, paroxetine, citalopram, and sertraline.

The nicotine in the device is present in the reservoir at a subsaturated condition (i.e. less than unit activity) such that no undissolved nicotine is present in the reservoir. If other agents are present in the device, they are preferably present fully dissolved, but can be present in undissolved form so long as the end product displays the proper degree of transparency.

In the present invention, nicotine and optionally other agents to be co-administered are delivered through the skin or other body surface at a therapeutically effective rate for a predetermined time period which for nicotine is preferably 16-24 hours.

The transdermal therapeutic devices of the present invention are prepared in a manner known in the art, such as by those procedures described in the transdermal device patents listed previously herein.

The following example is offered to illustrate the practice of the present invention and is not intended to limit the invention in any manner.

EXAMPLE 1

Various commercially available transdermal patches were tested to determine their transparency and compared to the transparent nicotine patches according to this invention. The nicotine patches were prepared as set forth in Example IV of U.S. Pat. No. 5,004,610 with a PET/EVA (SCOTCHPAK® 1220 film, 3M, Minneapolis, Minn.) or SARANEX® film (Dow Chemical Company, Midland, Mich.) backing substituted for the SCOTCHPAK 1006 film backing. The light transmitted through the various systems was measured by a MACBETH 1500/Plus color measurement system (Kollmorgem Instruments Corp., Newburgh, N.Y.). Table 1 shows the Opacity Index, which is the percentage of incidental light which is absorbed by passage through the device, for the various systems tested.

TABLE 1

Patch Opacity

| Patch | Opacity Index |
|---|---|
| MINITRAN ® | 48.6% |
| ALORA ® | 20.21% |
| FEMPATCH ® | 35.11% |
| CLIMARA ® | 19.33% |
| Ex. 1 - Nicotine with SARANEX ® backing | 17.04% |
| Ex. 1 - Nicotine with PET/EVA backing | 19.66% |

The MINITRAN® nitroglycerine system is clearly visible from a distance of about 5 feet, whereas the FEMPATCH® patch is significantly less noticeable. The ALORA®, CLIMARA® and NICODERM® patches, however, are extremely inconspicuous. Accordingly, transdermal devices according to this invention should have an Opacity Index less than 48.6%, preferably less than 35.11%, more preferably less than 20%.

Having thus generally described our invention and preferred embodiments thereof, it is apparent that various modifications and substitutions will be apparent to workers skilled in the art. These modifications and substitutions can be made without departing from the scope of our invention which is limited only by the following claims.

The invention claimed is:

1. A device for the transdermal administration of nicotine comprising:
   a backing layer formed from a material selected from the group consisting of PET/EVA laminates, HDPE/EAA/nylon/EAA multilaminate and a film comprising a graft copolymer formed from about 73-77% acrylonitrile and from about 23-27% methyl acrylate copolymerized in the presence of about 8-10 parts by weight of butadiene/acrylonitrile copolymers containing approximately 70% by weight of polymer units derived from butadiene,
   a drug reservoir layer containing nicotine carried by the backing layer, and
   an adhesive for maintaining the device in nicotine transmitting relationship with the skin,
   wherein the device is sufficiently transparent to permit the skin of the subject to which it is applied to be visible through the device.

2. The device according to claim 1, wherein the backing has a nicotine permeability of less than about 1.0 μg/cm$^2$/hr.

3. The device according to claim 1, wherein the backing has a nicotine permeability of less than 0.5 μg/cm$^2$/hr.

4. The device according to claim 2, wherein the backing has a solubility for nicotine of less than about 1 wt%.

5. The device according to claim 3, wherein the backing has a solubility for nicotine of less than about 0.1 wt%.

6. The device according to claim 4, wherein the device has an Opacity Index of less than about 48.6%.

7. The device according to claim 6, wherein the device has an Opacity Index of less than 35.11%.

8. The device according to claim 6, wherein the device has an Opacity Index of less than 20%.

9. The device according to claim 1, wherein the device provides delivery of nicotine for a period of 18-24 hours.

\* \* \* \* \*